United States Patent [19]
Gausepohl

[11] Patent Number: 6,143,012
[45] Date of Patent: *Nov. 7, 2000

[54] INTRAMEDULLARY AWL ASSEMBLY FOR PREPARATION FOR A FEMORAL-STYLE NAILING

[75] Inventor: Thomas Gausepohl, Cologne, Germany

[73] Assignee: Orthofix S.r.l., Bussolengo Verona, Italy

[ * ] Notice: This patent issued on a continued prosecution application filed under 37 CFR 1.53(d), and is subject to the twenty year patent term provisions of 35 U.S.C. 154(a)(2).

[21] Appl. No.: 09/072,033

[22] Filed: May 4, 1998

[30] Foreign Application Priority Data

May 6, 1997 [DE] Germany ............................ 197 190 52

[51] Int. Cl.⁷ .................................................... A61B 17/16
[52] U.S. Cl. ................................ 606/185; 606/96; 606/67
[58] Field of Search ................................ 606/96, 104, 99, 606/102, 184, 185, 67

[56] References Cited

U.S. PATENT DOCUMENTS

| | | | |
|---|---|---|---|
| 5,030,219 | 7/1991 | Matsen, III et al. | 606/53 |
| 5,037,423 | 8/1991 | Kenna | 606/88 |
| 5,700,267 | 12/1997 | Urbanski | 606/86 |

FOREIGN PATENT DOCUMENTS

| | | |
|---|---|---|
| 0440991 | 8/1991 | European Pat. Off. . |
| 8309912 | 4/1983 | Germany . |
| 8813655 | 10/1988 | Germany . |
| 8914852 | 12/1989 | Germany . |
| 2324967 | 11/1998 | United Kingdom . |

OTHER PUBLICATIONS

Pfeil, "Heidelberg External Fixation, Unilateral Fixation Techniques in Limb Deformity Corrections," George Thieme Verlag, 1998 Wandrey trans. (1st. ed. 1994), 48 pages (especially p. 23).

PD Dr. Dietmar Pennig, "The Pennig Dynamic Wrist Fixator, ORTHOFIX®, Operative Technique, Fractures of the Distal Radius and New: Radial Osteotomies", Orthofix Srl., Mar. 25, 1993, 47 pages.

*Primary Examiner*—Michael Buiz
*Assistant Examiner*—David O. Reip
*Attorney, Agent, or Firm*—Hopgood, Calimafde, Kalil & Judlowe, LLP

[57] ABSTRACT

The invention relates to an intramedullary awl assembly for opening the bone upon a femur nailing with a guide of a guide tool equipped with a hand grip, and an awl with a working tip equipped with an actuating handle. The guide is formed by an angle plate which is arranged on the end of the guide tool opposite the hand grip. The angle plate has a guide hole in the one arm, and an anchoring tip provided on the side of the other arm facing the bone. A shank of the guide tool acts on the top of the other arm in alignment with the central axis of the anchoring tip.

22 Claims, 5 Drawing Sheets

INTRAMEDULLARY AWL ASSEMBLY FOR PREPARATION FOR A FEMORAL-STYLE NAILING

BACKGROUND OF THE INVENTION

The present invention relates to an intramedullary awl assembly for opening bone tissue of a patient's femur, in preparation for an ensuing procedure, as to install an intramedullary nail in the femur.

Intramedullary awls are known and serve to open the bone in order then to be able to effect a femoral-style nailing in which a stainless steel nail, having for instance a clover-leaf or U-shaped cross section, can be inserted into the medullary cavity under control of an X-ray, for example, in the case of a fracture of a long bone. Before insertion of the nail, the medullary cavity situated in the middle two-thirds of the femur bone is opened by a drill or reamer. Before insertion of the reamer, it is necessary that the bone be first provided with a corresponding opening by means of an awl at the proximal end of the bone. Thereafter, in connection with insertion of the reamer, a guide wire for guiding the medullary reamer can be inserted through this opening. The opening in the bone produced by the awl is in coaxial alignment with the longitudinal axis of the medullary cavity in the region of the fossa between the greater trochanter and femoral head.

In DE-U 89 14 852 there is described an intramedullary awl which consists of two tools, namely, the awl and a guide tool. The guide tool has a receiving socket by which the working tip of the intramedullary awl can be guided. The receiving socket with the tip of the intramedullary awl is introduced into the hollow space between the greater trochanter and femoral head, bounded in part by the femoral neck, enabling the receiving socket to provide directional support for the awl to puncture the wall of the bone and enter its interior beneath the wall of the bone. After removal of the intramedullary awl from the opening in the bone produced by it, the receiving socket may remain in the hollow space between the greater trochanter and femoral head so that the patient's adjacent musculature does not again close the opening. In this way, easy introduction of the guide wire for the intramedullary reamer is made possible.

One problem in the case of the known tools is that an exact alignment of the actual guidance or orienting support for the working tip of the intramedullary awl is difficult. Such alignment is necessary since the intramedullary awl preferably passes through the bone precisely along and in coaxial alignment with the longitudinal axis of the medullary cavity in order thereby to obtain a guidance reference that is aligned with the medullary cavity in that such a guidance reference is needed for insertion of the guide wire and also for use of the drill or reamer tooling which is to expand the bore in the bone to a size which will accept insertion of an intramedullary nail.

BRIEF STATEMENT OF THE INVENTION

The primary object of the invention is to provide a guide-positioning device for improved guidance of the working tip of an intramedullary awl, wherein easy centering and alignment of the guide opening is facilitated in X-ray viewing needed to establish a correct positioning for the device; and having established the correctly positioned location of the device, it is a further object that the device shall have provision for reliable retention of the correctly aligned guide.

A still further object of the invention is to provide an intramedullary awl for use in combination with the guide-positioning device wherein the awl enabling manipulation of the awl laterally of the bone.

A still further object of the invention is to provide a method for using the guide-positioning device and intramedullary awl to puncture the cortical and cancellous bone to create a passage from the outer surface of the bone to the medullary cavity.

In meeting the foregoing objects, the invention provides a guidance device for the working tip of an intramedullary awl, wherein the device derives support from engagement with the greater trochanter; this engagement is such that rotary movement, rotary adjustment, pivoting or swivelling of the guidance device, to bring a guide bore of the device into alignment with the medullary cavity is then possible on the support. The guidance device may be suitably aligned by pushing a portion of the anchoring tip into the outer surface of the bone such that a clearance exists between the angle plate and outer surface of the bone. Due to the clearance, such rotary movements and adjustments do not produce rubbing between the inside of the angle plate and the outside of the bone. The guidance device can thereby be aligned such that the working tip of the awl can be easily driven into the bone. The awl and guidance device may be driven into the bone by different individuals.

It is important that the shank of the guide tool be aligned with the longitudinal axis of the anchoring tip on the bottom of the angle plate. By having the shank so aligned and by properly directing the handle of the guide tool, the anchoring tip may be driven into the bone and held in it with limited swinging movements or tilting between the guidance device and the bone, while making it possible for turning, rotary or swivelling movements of the guidance device around the anchoring tip the longitudinal axis of which provides a swivel axis.

While in the foregoing, an example of the invention has been explained having a single anchoring tip, it lies within the scope of the invention to provide several anchoring tips. Preferably, if there are multiple anchoring tips, the central anchoring tip is aligned with the portion of the shank of the guide tool fixed to the angle plate. Such a central anchoring tip is furthermore preferably longer than the other anchoring tips so that, despite the use of several anchoring tips, easy turning provided by the above-described rotary movement is possible by limited insertion of the central anchoring tip into the outer bone surface leaving a clearance between the shorter anchoring tips and outer bone surface. Better fixing of the working tool or angle plate is then obtained by further pressing the shorter anchoring tips into the outer bone surface.

The angle formed by the two arms of the guide or angle plate is preferably 135°, and thus ideally fits the outer contour of the greater trochanter.

The awl has a curved shank enabling the awl to be manipulated laterally of the bone.

BRIEF DESCRIPTION OF THE DRAWINGS

The invention will be illustratively described in detail in conjunction with the accompanying drawings, and one embodiment of the invention will be explained below with reference to the drawings, in which.

Corresponding reference characters indicate corresponding parts throughout the several views of the drawings.

DETAILED DESCRIPTION

Figure 1:
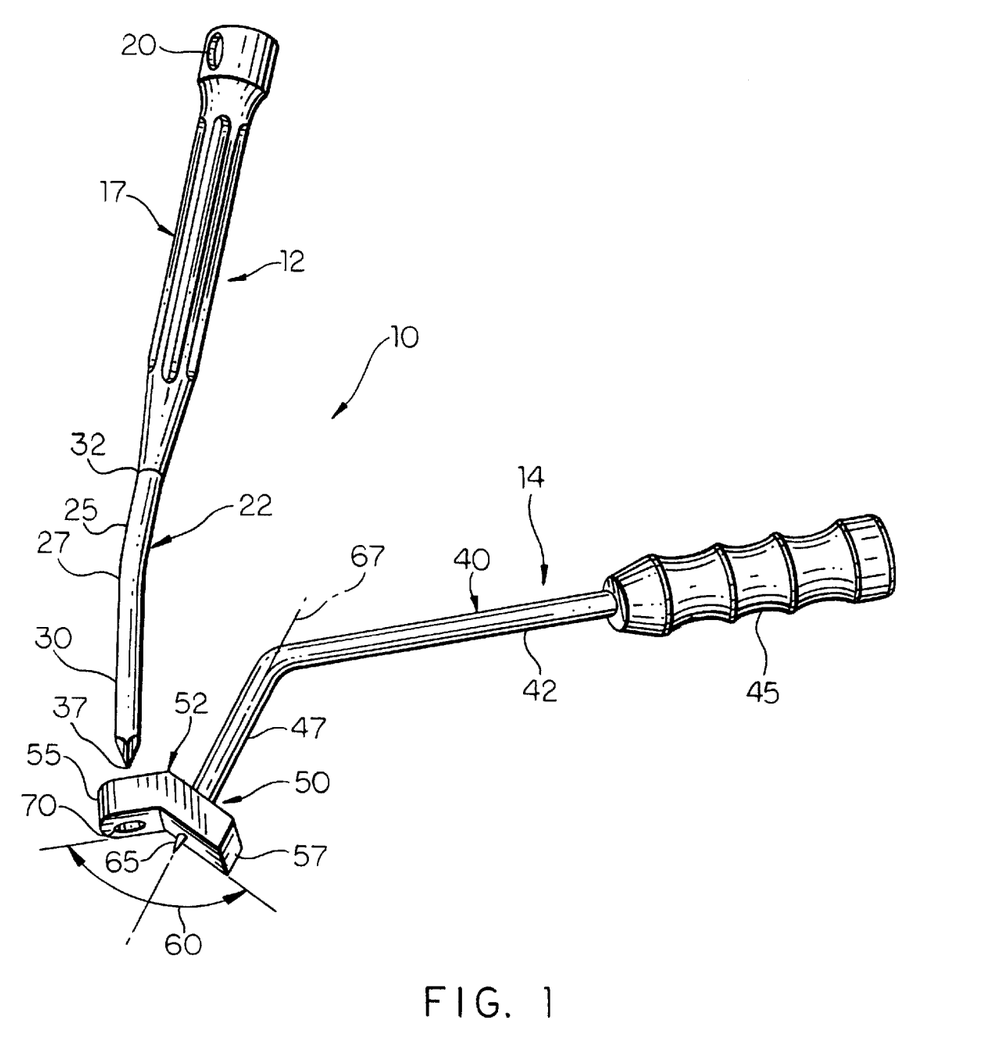
FIG. 1 is a perspective view of the awl and guide tool forming the intramedullary awl assembly.

In the drawings, the two tools forming the intramedullary awl assembly 10, i.e., awl 12 and a guide tool, guidance device, guide tool or guide jig 14, are shown in FIG. 1. It will be understood that awl 12 and guide jig 14 may be included in a kit.

Figure 2:
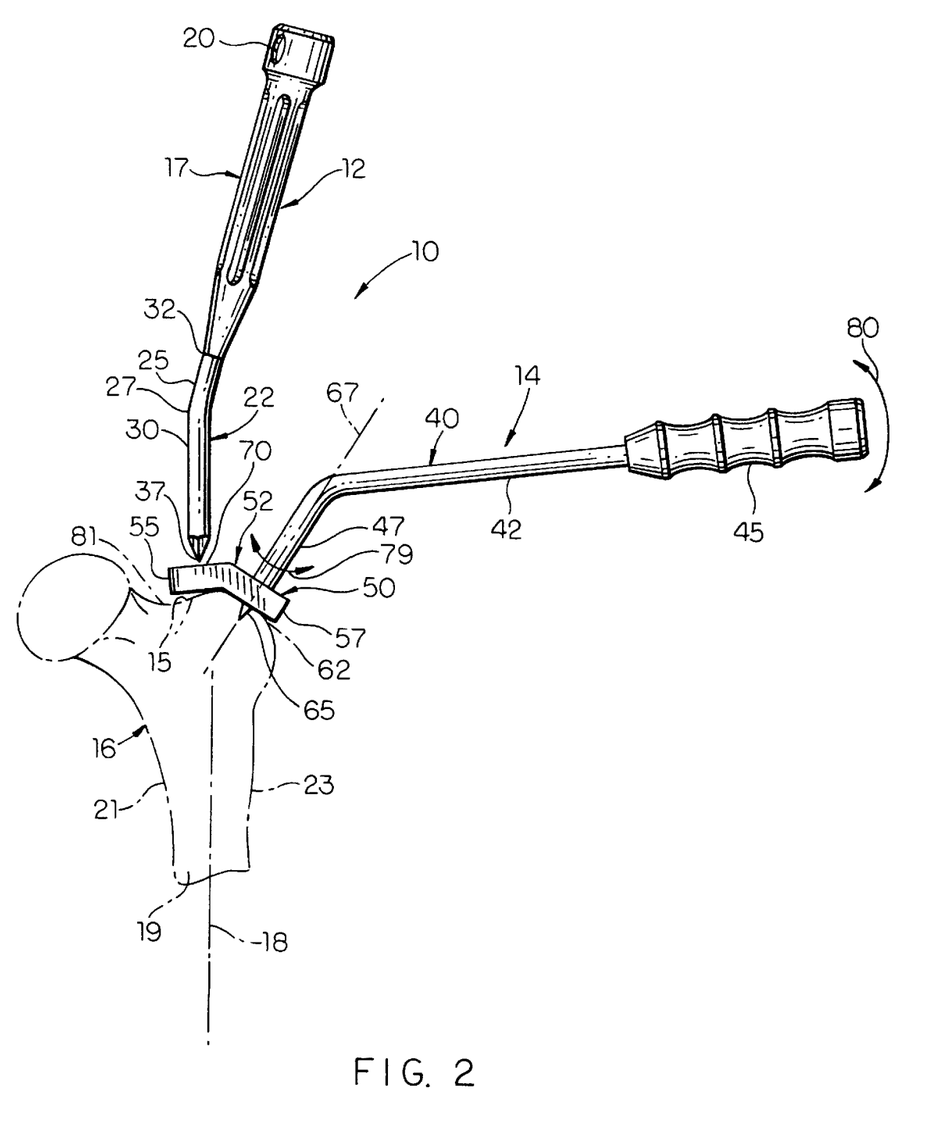
FIG. 2 is an anterior view of a left femur bone showing the intramedullary awl assembly of FIG. 1 applied to the greater trochanter of the femur bone, the bone being shown in phantom and the anchoring tip of the guide jig being shown driven into the bone.
Figure 5:
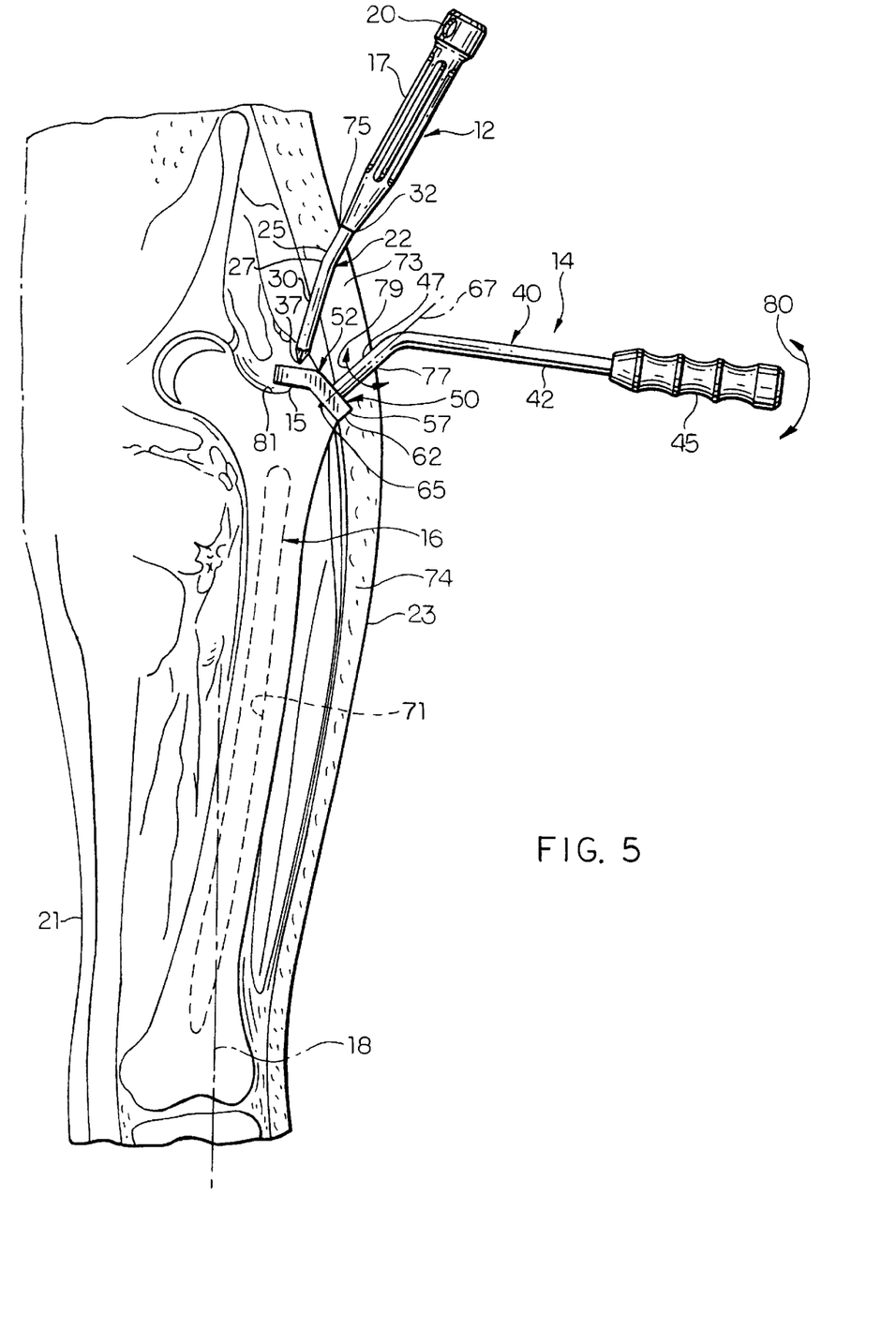
FIG. 5 is a view of the intramedullary awl assembly of FIG. 1 applied to the femur bone surrounded by the soft tissue of the leg.
Figure 6:
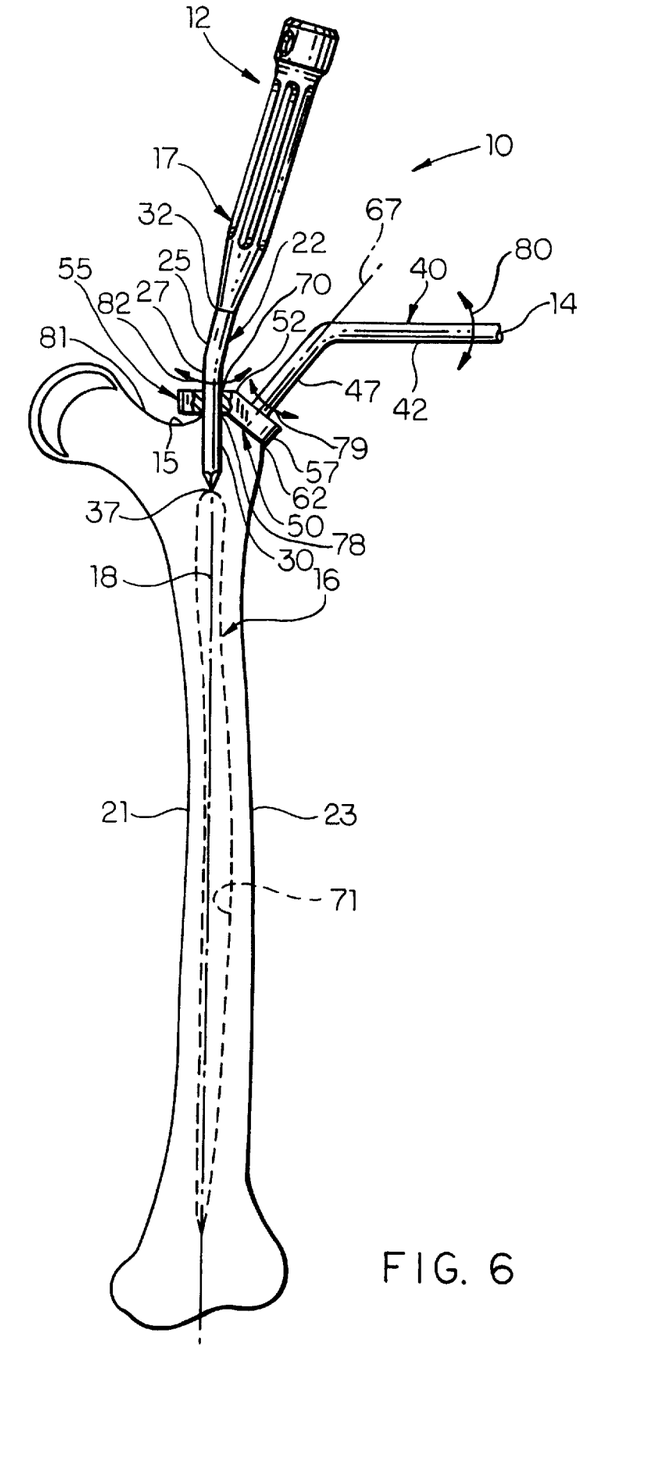
FIG. 6 is an enlarged schematic view of portions of the intramedullary awl assembly of FIG. 1 applied to the femur bone to illustrate the engagement between the awl and shoulder of the greater trochanter.

FIGS. 2, 5 and 6 are views in frontal planes of femur bone 16. Perpendicular to the frontal planes are sagittal planes of femur bone 16, one of which is indicated by reference character 18 in FIGS. 2, 5 and 6. Femur bone 16 has an anterior surface 19 opposite a posterior surface, and opposing medial and lateral surfaces 21, 23.

Awl 12 includes a one-piece shank 22 including generally straight proximal and distal portions 25, 30 which are axially separated by a curved portion 27. The bend in curved portion 27 is such that the longitudinal central axes of proximal and distal portions 25, 30 are inclined relative to one another. A pointed working tip 37 is formed in the end of distal portion 30. A longitudinal section of proximal portion 25 which is longitudinally spaced from curved portion 27 is formed for grasping, such as by having an actuating handle 17 fixed to it. Actuating handle 17 includes a transverse bore 20 into which is inserted an elongate tool for rotating the handle, described herein below.

The dimension between the base 32 of actuating handle 17 and working tip 37, in a direction parallel to the longitudinal central axis of distal portion 30, is at least 10 to 12 centimeters (cm), which is not less than the typical thickness of the cortical and cancellous bone underlying fossa 15 which is punctured by shank 22 of awl 12, described herein below. The cortical bone constitutes the outer surface of femur bone 16, and the cancellous bone underlies the cortical bone. Underlying fossa 15, the thickness of the cortical bone is typically less than 1 mm and the thickness of the cancellous bone is approximately 6 to 10 cm.

Guide jig 14 has a manipulating means including a one-piece shank 40 having generally straight proximal and distal portions 42, 47 the longitudinal central axes of which are inclined relative to one another. A longitudinal section of proximal portion 42 which is longitudinally spaced from distal portion 47 is formed for grasping, such as by having a hand grip 45 fixed to it.

Guide jig 14 also includes a guide 50 including or developed as a template 52 constituted by an angle plate provided at or fixed to the end of distal portion 47. As shown in FIG. 2, template 52 of the guide 50 has two arms 55, 57 which are arranged at an angle to each other and enclose an angle 60 of about 135° on the lower or distal sides thereof facing the femur bone 16. Angle 60 of about 135° enables the joint between arms 55, 57 of template 52 to sit squarely on greater trochanter 62, as shown in FIG. 2. Distal portion 47 of guide jig 14 is fixed to and acts on the upper or proximal side of the arm 57 facing away from greater trochanter 62.

On the distal side of the arm 57 facing greater trochanter 62 is arranged and fixed an anchoring means defined by anchoring tip 65. The longitudinal central axis of anchoring tip 65 defines an anchor axis 67 which is coaxially aligned with the longitudinal central axis of distal portion 47 of shank 40 of the guide jig 14.

Formed in the arm 55 of the template 52 is a guide hole or bore 70 the size or diameter of which is adapted to the working tip 37 of the awl 12 such that, when the shank 22 of awl 12 is inserted through the guide hole, a small radial clearance exists between the shank and walls of guide bore 70.

Without going beyond the scope of the invention, it is, of course, possible to use an elongate member (similar to working tip 37) fixed to template 52 and inserted into the passage formed in the cortical and cancellous bone by working tip 37 after removal of the working tip. A closing of the opening formed by the working tip 37 is thereby obstructed and a similar closing of the muscles and subcutaneous fatty tissue is obstructed by hooks which hold the wound open.

Figure 3:
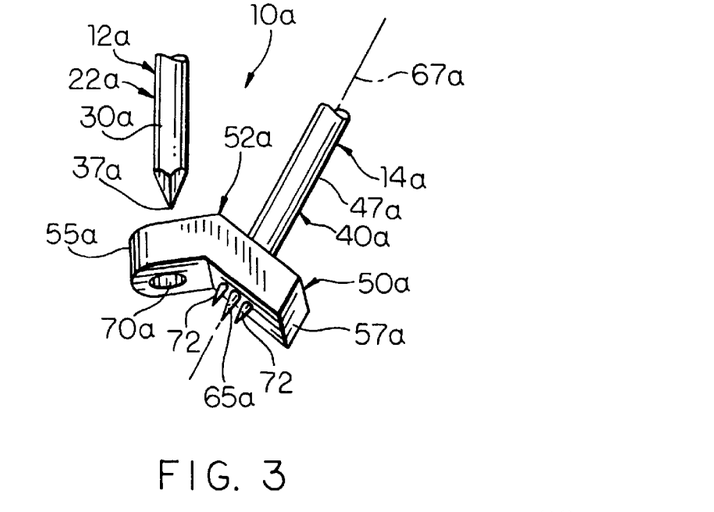
FIG. 3 is an enlarged view corresponding to FIG. 1 showing an alternative embodiment of the template including central and outer anchoring tips.
Figure 4:
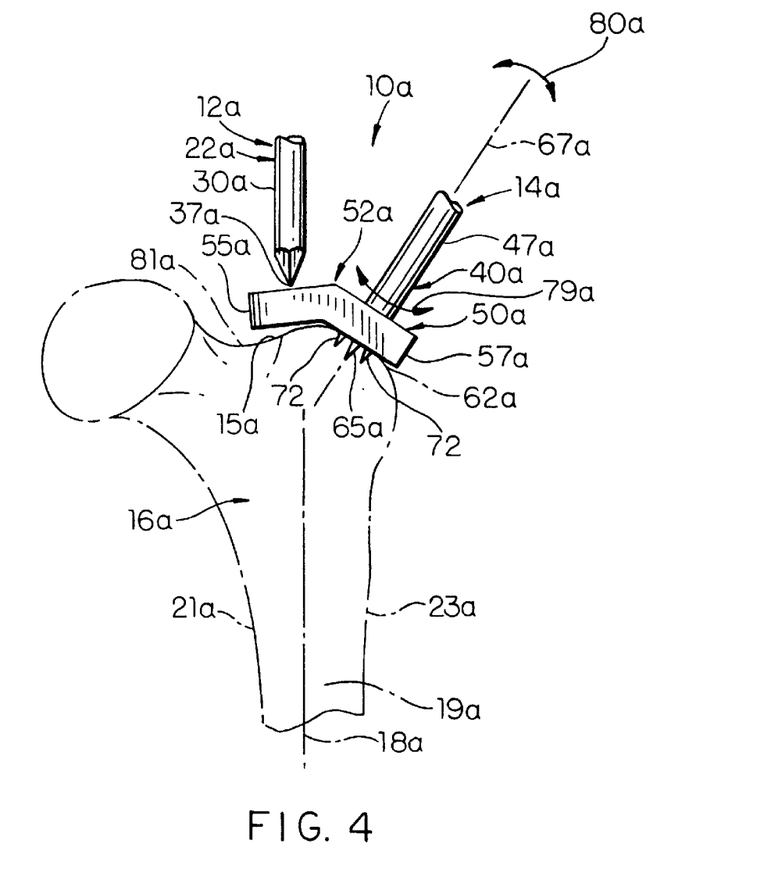
FIG. 4 is an enlarged view corresponding to FIG. 2 showing the template of FIG. 3 including central and outer anchoring tips driven into the femur bone.

FIGS. 3 and 4 illustrate an alternative embodiment of guide jig 14a in which a central anchoring tip 65a and a plurality of outer anchoring tips 72 are fixed to the distal side of arm 57a placed on greater trochanter 62a. The parts of guide jig 14a corresponding to guide jig 14 are represented by the reference characters used in FIGS. 1 and 2 with the addition of the suffix a in FIGS. 3 and 4. Central anchoring tip 65a is located generally equidistant from outer anchoring tips 72 in the plane of the surface of arm 57 which contacts greater trochanter 62. The longitudinal dimension of central anchoring tip 65a is greater than those of outer anchoring tips 72 each of which has the generally the same longitudinal dimension. The longitudinal central axis of central anchoring tip 65a defines an anchor axis 67a which is coaxially aligned with the longitudinal central axis of distal portion 47a of guide jig 14a.

FIG. 2 diagrammatically shows the use of the guide jig 14 on femur bone 16. In this connection, the template 52 is placed on the outer or proximal side of the greater trochanter 62, it being held on its position by the anchoring tip 65 on the proximal side of the greater trochanter. Despite this fixing in position, rotary movements around the longitudinal central axis of the anchoring tip 65 are possible, while shifting or translation of template 52 is limited in a plane which is perpendicular to the axis of the anchoring tip, such as the plane of arm 57. This permits an exact alignment of the opening to be produced by the working tip 37 of the awl 12. In this way, the alignment of the opening or passage in the cortical and cancellous bone of femur bone 16 with its medullary cavity 71 is facilitated with the use of an X-ray image intensifier.

More specifically, a method for using the intramedullary awl assembly 10 is illustrated in FIGS. 2, 5 and 6. The method includes the step of creating an elongate incision 73 having proximal and distal ends 75, 77 in the lateral outer surface of soft tissue 74 surrounding femur bone 16 proximal to greater trochanter 62, shown in FIG. 5. Proximal and distal ends 75, 77 are positioned relative to greater trochanter 62 such that, when incision 73 is opened and spread, shanks 22, 40, including their respective proximal portions 25, 42, may extend through the incision, as shown in FIG. 5. Soft tissue 74 is then opened and spread to provide access to greater trochanter 62 and the region of fossa 15 to be punctured. The spreading of soft tissue 74 is sufficient to allow the positioning of awl 12 and guide jig 14 within incision 73, as shown in FIG. 5. Soft tissue 74 is held open by hooks or the like.

Hand grip 45 of guide jig 14 is then grasped and manipulated to give proximal portion 42 a slightly downward or distal cant, or a generally horizontal orientation, with template 52 being positioned distally of it, as shown in FIGS. 2, 5 and 6. Continuing to grasp hand grip 45, template 52 is inserted through incision 73 adjacent to distal end 77 and directed medially, relative to soft tissue 74, toward greater trochanter 62. Arm 57 is placed above the upper or proximal surface of greater trochanter 62 such that the pointed end of anchoring tip 65 lightly rests on it and the central longitudinal axis of guide bore 70 intersects the region of fossa 15 adjacent to the greater trochanter to be punctured by working tip 37, as shown in FIGS. 2 and 6.

Actuating handle 17 of awl 12 is then grasped and manipulated so that the center of curvature of curved portion 27 of the awl is positioned distally of shank 22, as viewed in FIGS. 2, 5 and 6. Shank 22 is inserted through incision 73 and positioned such that proximal portion 25 is adjacent proximal end 75 and working tip 37 extends through guide bore 70 and lightly engages the region on fossa 15 to be punctured. The inclinations between proximal and distal portions 25, 30, 42, 47 of awl 12 and guide jig 14 enables actuating handle 17 and hand grip 45 to be held laterally of incision 73 and the lateral surface 23 of the soft tissue 74, as shown in FIG. 5.

Working tip 37 of awl 12, extending through guide bore 70, is precisely located on the entry point on fossa 15 to be punctured by positioning the working tip relative to the fossa in a frontal plane and a sagittal plane, parallel to sagittal plane 18. Working tip 37 is positioned in the sagittal plane manually and visually through incision 73. Working tip 37 is positioned in the frontal plane using an X-ray image intensifier positioned to face either the anterior or posterior surface of femur bone 16. When working tip 37 contacts the entry point of fossa 15 and the longitudinal central axis of shank 22 is contained in the frontal plane, distal portion 30 of awl 12 contacts the medial shoulder 78 of greater trochanter 62, as shown in FIG. 6.

With working tip 37 engaging the entry point of fossa 15 to be punctured, template 52 is positioned so that the longitudinal central axis of guide bore 70 is coaxially aligned with the longitudinal central axis of distal portion 30 of awl 12. Initially, template 52 is so aligned by grasping hand grip 45 to lift anchoring tip 65 proximally from greater trochanter 62 sufficiently to disengage it from femur bone 16. Hand grip 45 is then manipulated to bring the longitudinal central axis of guide bore 70 into approximate coaxial alignment with the longitudinal central axis of distal portion 30 of awl 12.

Hand grip 45 is then forcibly directed in a generally distal direction toward greater trochanter 62, and more specifically, in a direction parallel to the central longitudinal axis of distal portion 47 of shank 40. As a result, a limited longitudinal portion of anchoring tip 65 is driven into greater trochanter 62 such that a clearance parallel to anchor axis 67 remains between femur bone 16 and the side of template 52 facing it. The insertion of anchoring tip 65 into greater trochanter 62 restricts translation or shifting of the arm 57 of template 52 relative to femur bone 16 in the plane of arm 57 which is perpendicular to anchor axis 67.

More precise coaxial alignment of the longitudinal central axes of distal portion 30 and guide bore 70 may then be obtained by rotating hand grip 45 about anchor axis 67. Such rotation produces concomitant angular displacement of arm 57 about anchor axis 67 indicated by reference character 79 in FIGS. 2, 5 and 6. The clearance between template 52 and greater trochanter 62 limits rubbing of the template against femur bone 16.

Further such precise alignment may be obtained by tilting hand grip 45 relative to anchoring tip 65 resulting in concomitant tilting of the longitudinal central axis of guide bore 70. Such tilting of hand grip 45 may be in the frontal plane, indicated by reference character 60 in FIGS. 2, 5 and 6, in a sagittal plane (parallel to sagittal plane 18) or in a plane oblique to those planes, to provide variable adjustment to the inclination of the longitudinal central axis of guide bore 70.

Upon aligning template 52 such that the longitudinal central axes of guide bore 70 and distal portion 30 of awl 12 are coaxially aligned, hand grip 45 of guide jig 14 is forcibly directed generally distally toward greater trochanter 62 in a direction parallel to the longitudinal central axis of distal portion 30 to drive the entire length of anchoring tip 65 into the greater trochanter. Preferably, a force so directed, though having a reduced magnitude, is continuously applied to hand grip 45 to maintain the alignment of guide jig 14.

Awl 12 is then laterally inclined, as viewed in FIGS. 2, 5 and 6, using the X-ray image intensifier, so that the longitudinal central axes of distal portion 30 and medullary cavity 71 of femur bone 16 are approximately coaxially aligned in the frontal plane. Actuating handle 17 is then grasped and its end forcibly directed generally toward fossa 15, as by a hammer, mallet or the like. More specifically, the direction of the force applied to actuating handle 17 is coaxial with the longitudinal central axis of proximal portion 25 resulting, for example, from squarely striking the end of the actuating handle.

The direction of the force applied to actuating handle 17, which is coaxial with the longitudinal central axis of proximal portion 25, is inclined relative to the longitudinal central axis of distal portion 30 due to curved portion 27. As a result, a small component of the force directs distal portion 30 in a medial direction toward neck 81 of femur bone 16. The larger component of the force directs distal portion 30 distally through the cortical and cancellous bone underlying fossa 15 toward medullary cavity 71.

The medial component of the force causes distal portion 30 to bear against an internal portion of the cortical and cancellous bone of fossa 15 adjacent neck 81. Any resulting deformation of the bone is slight because of the limited medial translation of distal portion 30 relative to fossa 15 permitted by the small radial clearance between the distal portion and walls of guide bore 70. Arm 55 is, in turn, supported to resist medial translation relative to fossa 15 by the insertion of anchoring tip 65 into greater trochanter 62, and the medial or horizontal component of the abutment of inclined arm 57 against the greater trochanter. The small radial clearance between the walls of guide bore 70 and distal portion 30 also maintains the working tip 37 in precise contact with the entry point on fossa 15 during initial puncturing of it by the working tip.

Approximately 3 to 5 cm of shank 22 including working tip 37 is driven into the cortical and cancellous bone underlying fossa 15. The longitudinal central axes of distal portion 30 and medullary cavity 71 remain in approximate coaxial alignment in the frontal plane.

The X-ray image intensifier is then relocated to a lateral position relative to femur bone 16 so as to face lateral surface 23 of soft tissue 74 surrounding the femur bone. The alignment in a sagittal plane (parallel to sagittal plane 18) of the longitudinal central axes of distal portion 30 and medullary cavity 71 of femur bone 16 is visually monitored using the X-ray image intensifier. After insertion of shank 22 through the entry point on fossa 15 limits, misalignment of the shank in the frontal plane is limited by the resting of it against the shoulder of greater trochanter 62, as shown in FIG. 6.

Actuating handle 17 is rotated about its longitudinal axis to concomitantly rotate distal portion 30 about its longitudinal central axis in the direction indicated by reference character 82 in FIGS. 5 and 6. Actuating handle 17 may be so rotated manually or by inserting an elongate tool through transverse bore 20 and applying a force to the tool perpendicular to its longitudinal central axis. Actuating handle 17 is rotated sufficiently to produce an angular displacement of 90° of distal portion 30 in direction 82 such that the actuating handle is anteriorly inclined.

Actuating handle 17 is then grasped and forcibly driven into the cortical and cancellous bone underlying fossa 15, as described herein above. The rotation of shank 22 causes a change in the direction of the medial or horizontal force imparted to distal portion 30, described herein above, resulting the inclination between the longitudinal central axes of proximal and distal portions 25, 30. For example, a 90° rotation of the distal portion 30 in direction 82 such that the actuating handle is anteriorly inclined results in the horizontal force to be directed toward the posterior. Such force is resisted by the engagement between anchoring tip 65 and greater trochanter 62. If the force has a medial component, such component is also resisted by the abutment of inclined arm 57 against the greater trochanter.

If the longitudinal central axes become misaligned, then actuating handle 17 is rotated generally about its longitudinal central axis thereby causing, in turn, rotation of distal portion 30 about its longitudinal axis to bring the longitudinal central axis of distal portion 30 into coaxial alignment with the longitudinal central axis of medullary cavity 71 of femur bone 16 in a sagittal plane, parallel to sagittal plane 18.

Shank 22 is continued to be forcibly driven through fossa 15 until working tip 37 reaches medullary cavity 71 thereby producing a passage through the cortical and cancellous bone underlying fossa 15. Since the dimension between the base 32 of actuating handle 17 and working tip 37, in a direction parallel to the longitudinal central axis of distal portion 30, is at least equal to the thickness of the cortical and cancellous bone underlying fossa 15, working tip 37 reaches medullary cavity 71 before or contemporaneously with the base of the actuating handle reaching template 52 adjoining guide bore 70. The passage formed in the cortical and cancellous bone underlying fossa 15 leading to medullary cavity 71 is generally straight.

After completion of the passage through the cortical and cancellous bone underlying fossa 15, template 52 is maintained on greater trochanter 62 in generally the same position as for supporting shank 22 of awl 12 during insertion of it to form the passage to medullary cavity 71. The passage through the cortical and cancellous bone underlying fossa 15 to medullary cavity 71 may thereby be identified after, for example, removal from it of shank 22 of awl 12 since the central longitudinal axes of the medullary cavity and guide bore 70 are coaxial. Incision 73 in soft tissue 74 is held open by hooks.

Shank 22 of awl 12 is removed from the passage through the cortical and cancellous bone underlying fossa 15 for ultimate insertion of a nail into it. Before insertion of the nail into the passage in femur bone 16, a reamer, and possibly a guide wire for it, may be inserted into the passage for further boring of it.

The passage through the cortical and cancellous bone underlying fossa 15 to the medullary cavity 71 produced by awl 12 is preferably maintained, until needed for example to insert a reamer or guide wire for it, by leaving shank 22 extending through incision 73 and in the passage in the cortical and cancellous bone underlying fossa 15 to medullary cavity 71.

A template 52a having a central anchoring tip 65a and a plurality of outer anchoring tips 72, as shown in FIGS. 3 and 4, is used in a similar manner as template 52 described herein above, except as follows. The hand grip of guide jig 14a, similar to hand grip 45, is grasped and manipulated to insert template 52a through the incision in the soft tissue adjacent to the greater trochanter, similar to incision 73 adjacent to greater trochanter 62a. Shank 40a of guide jig 14a is positioned adjacent to the distal end of the incision, similar to distal end 77 of incision 73. Arm 57a is placed above the proximal surface of greater trochanter 62a such that the pointed end of central anchoring tip 65a lightly rests on it and the central longitudinal axis of guide bore 70a intersects the region of fossa 15a adjacent to the greater trochanter to be punctured by working tip 37a, as described herein above for anchoring tip 65 of template 52.

When awl 12a is positioned relative to greater trochanter 62a such that working tip 37a contacts the entry point on fossa 15a in a similar manner as described herein above for template 52, hand grip 45 is grasped and manipulated to lift central anchoring tip 65a in a proximal direction relative to greater trochanter 62a sufficiently to disengage it from femur bone 16a. Hand grip 45a is then manipulated to bring the longitudinal central axis of guide bore 70a into approximate coaxial alignment with the longitudinal central axis of distal portion 30a of awl 12a.

Hand grip 45a is then directed by a force which is parallel to the central longitudinal axis of distal portion 30a of shank 22a, as described above for template 52. The longitudinal portion of central anchoring tip 65a extending beyond the pointed ends of outer anchoring tips 72 is driven into greater trochanter 62a such that a clearance parallel to anchor axis 67a remains between the greater trochanter and pointed ends of the outer anchoring tips.

As described herein above, arm 57a may be rotated about anchor axis 67a in the direction 79a to obtain more precise coaxial alignment of the longitudinal central axis of guide bore 70a with that of distal portion 30a. The clearance between the pointed ends of outer anchoring tips 72 and greater trochanter 62a limits scratching of the pointed ends of the outer anchoring tips against femur bone 16a which may irritate it. Further such precise alignment may be obtained by tilting hand grip 45a relative to central anchoring tip 65a in the direction 80a, in a similar manner as described herein above for similar tilting about anchoring tip 65. The insertion of the longitudinal portion of central anchoring tip 65a into greater trochanter 62a restricts translation or shifting of arm 57a of template 52a relative to femur bone 16a in the plane of arm 57a which is perpendicular to anchor axis 67a, in a similar manner as described herein above for template 52.

When template 52a is aligned, by the swivelling 79a about anchor axis 67a, and tilting 80a about anchoring tip 65a such that the longitudinal central axis of guide bore 70a is coaxial with the longitudinal central axis of distal portion 30a of awl 12a, the hand grip of guide jig 14a, similar to hand grip 45, is forcibly directed toward greater trochanter 62a in a similar manner as for driving anchoring tip 65 into the greater trochanter as described herein above. Sufficient force is applied to the hand grip to drive the inner portion of central anchoring tip 65a and the entire length of outer anchoring tips 72 into femur bone 16a.

Insertion of outer anchoring tips 72 into greater trochanter 62a provides a more stable connection between template 52a and the greater trochanter. This obstructs the template 52a from swivelling 79a about anchor axis 67a and swivelling about the longitudinal central axes of outer anchoring tips 72 relative to femur bone 16a. Insertion of outer anchoring tips 72 also provides added obstruction to swinging and tilting of guide jig 14a relative to femur bone 16a about central and outer anchoring tips 65a, 72 in the frontal plane in direction 80a, in a sagittal plane parallel to sagittal plane 18a, or in a plane oblique to those planes.

Additionally, insertion of outer anchoring tips 72 into greater trochanter 62a provides additional medial or horizontal support to arm 55a to resist horizontal displacement of distal portion 30a of awl 12a urged by the oblique attitude of the force imparted to the actuating handle, similar to actuating handle 17, relative to distal portion 30a, described herein above. Such horizontal displacement results from the inclination between the longitudinal central axes of the proximal portion of awl 12a, similar to proximal portion 25, and distal portion 30a. As described herein above, the direction of such horizontal displacement may change as a result of rotation of shank 22a.

The intramedullary awl assembly 10 of the invention is capable of numerous modifications and variants which fall within the scope of the accompanying claims. For example, the embodiments disclosed in FIGS. 1 to 6 are described for puncturing the fossa 15 of a femur bone 16 and forming a passage through the underlying cortical and cancellous bone which terminates in medullary cavity 71. It will be understood that the embodiments of FIGS. 1 to 6, and alternative embodiments of the intramedullary awl assembly 10 may be used to puncture other regions of femur bone 16 as well as other bones. And the dimensions, shapes and materials may also be modified without departure from the scope of the invention.

I claim:

1. An intramedullary awl assembly for opening a non-planar outer surface of a bone upon a femur nailing, comprising: a guide (50) of a guide tool (14) equipped with a handle (45) and an awl (12) equipped with an actuating grip (17) with S working tip (37), wherein
   (a) the guide (50) is formed by an angle plate (52) which is arranged on an end of the guide tool (14) lying opposite the handle (45);
   (b) the angle plate (52) having two arms (55, 57) each of which has a distal side, the distal sides forming with each other an angle (60) of less than 180°, one of the arms (55) having a guide hole (70); and
   (c) at least one anchoring tip (65) is arranged on the distal side of the other arm (57) facing the bone.

2. An intramedullary awl assembly according to claim 1, characterized in that only one anchoring tip (65) is provided.

3. An intramedullary awl assembly for opening a bone upon a femur nailing, comprising: a guide (50) of a guide tool (14) equipped with a handle (45) and an awl (12) equipped with an actuating grip (17) with working tip (37), wherein
   (a) the guide (50) is formed by an angle plate (52) which is arranged on an end of the guide tool (14) lying opposite the handle (45);
   (b) the angle plate (52) having two arms (55, 57) each of which has a distal side, one of the arms (55) having a guide hole (70); and
   (c) at least one anchoring tip (65) is arranged on the distal side of the other arm (57) facing the bone, characterized in that the arms (55, 57) each having a proximal side opposing the corresponding distal side, the shank (40) of the guide tool (14) being aligned on the proximal side of the arm (57) with a longitudinal central axis of the anchoring tip (65).

4. An intramedullary awl assembly for opening a bone upon a femur nailing, comprising: a guide (50) of a guide tool (14) equipped with a handle (45) and an awl (12) equipped with an actuating grip (17) with working tip (37), wherein
   (a) the guide (50) is formed by an angle plate (52) which is arranged on an end of the guide tool (14) lying opposite the handle (45);
   (b) the angle plate (52) having two arms (55, 57) each of which has a distal side, one of the arms (55) having a guide hole (70); and
   (c) only one anchoring tip (65) is arranged on the distal side of the other arm (57) facing the bone, characterized in that the arms (55, 57) each having a proximal side opposing the corresponding distal side, the shank (40) of the guide tool (14) being aligned on the proximal side of the arm (57) with a longitudinal central axis of the anchoring tip (65).

5. An intramedullary awl assembly for opening a bone upon a femur nailing, comprising: a guide (50) of a guide tool (14) equipped with a handle (45) and an awl (12) equipped with an actuating grip (17) with working tip (37), wherein
   (a) the guide (50) is formed by an angle plate (52) which is arranged on an end of the guide tool (14) lying opposite the handle (45);
   (b) the angle plate (52) having two arms (55, 57) each of which has a distal side, one of the arms (55) having a guide hole (70); and
   (c) at least one anchoring tip (65) is arranged on the distal side of the other arm (57) facing the bone, characterized in that the distal sides of the two arms (55, 57) of the angle plate (52) form with each other an angle (60) of about 135°.

6. An intramedullary awl assembly for opening a bone upon a femur nailing, comprising: a guide (50) of a guide tool (14) equipped with a handle (45) and an awl (12) equipped with an actuating grip (17) with working tip (37), wherein
   (a) the guide (50) is formed by an angle plate (52) which is arranged on an end of the guide tool (14) lying opposite the handle (45);
   (b) the angle plate (52) having two arms (55, 57) each of which has a distal side, one of the arms (55) having a guide hole (70); and
   (c) at least one anchoring tip (65) is arranged on the distal side of the other arm (57) facing the bone, characterized in that the one anchoring tip (65) is defined by one of several anchoring tips (65a, 72) arranged on the side of the other arm (57) facing the bone, one of the several anchoring tips (65a, 72) defining a central anchoring tip (65a) of greater length than the other anchoring tip (72).

7. A guide jig for an intramedullary awl comprising:

a template having two arms each of which has a distal side, said distal sides forming with each other an angle of less than 180°, one of the arms having a guide bore;

a means for anchoring said distal side of said other arm to a non-planar outer surface of a bone, said anchoring means having an anchor axis about which said template rotates relative to the bone when said template is anchored to the bone outer surface, said anchoring means limiting translation of said template relative to the bone outer surface in a plane perpendicular to said anchor axis when said template is anchored to the bone outer surface; and a means for manipulating said template to apply said anchoring means to the bone outer surface such that said guide bore is adjacent to a preselected entry point on the bone outer surface and the longitudinal central axis of said guide bore intersects the entry point, said guide bore radially supporting a shank of the awl inserted through it to direct the awl to puncture the bone outer surface at the entry point.

8. A guide jig according to claim 7 wherein said anchoring means comprises an elongate anchoring tip fixed to the surface of said template which, when said template is anchored to the bone outer surface, faces the bone outer surface, said anchoring tip having a pointed end and a longitudinal central axis defining said anchor axis, said template being anchored to the bone by driving said anchoring tip into the bone outer surface.

9. A guide jig for an intramedullary awl comprising:

a template having a guide bore;

a means for anchoring said template to the outer surface of a bone, said anchoring means having an anchor axis about which said template rotates relative to the bone when said template is anchored to the bone outer surface, said anchoring means limiting translation of said template relative to the bone outer surface in a plane perpendicular to said anchor axis when said template is anchored to the bone outer surface; and a means for manipulating said template to apply said anchoring means to the bone outer surface such that said guide bore is adjacent to a preselected entry point on the bone outer surface and the longitudinal central axis of said guide bore intersects the entry point, said guide bore radially supporting a shank of the awl inserted through it to direct the awl to puncture the bone outer surface at the entry point, said anchoring means comprising an elongate anchoring tip fixed to the surface of said template which, when said template is anchored to the bone outer surface, faces the bone outer surface, said anchoring tip having a pointed end and a longitudinal central axis defining said anchor axis, said template being anchored to the bone by driving said anchoring tip into the bone outer surface, said anchoring tip defining a central anchoring tip, said anchoring means further comprising an elongate outer anchoring tip fixed to the surface of said template which, when said template is anchored to the bone outer surface, faces the bone outer surface, the longitudinal central axes of said outer and central anchoring tips being parallel to one another, said outer anchoring tip having a pointed end and a shorter length relative to the length of said central anchoring tip, said template being further anchored to the bone by driving said outer anchoring tip into the bone outer surface.

10. A guide jig according to claim 9 wherein said anchoring means comprises a plurality of said outer anchoring tips the longitudinal central axes of which are equidistant from the longitudinal central axis of said central anchoring tip.

11. An intramedullary awl kit comprising:

an awl including
a shank having proximal and distal portions the longitudinal central axes of which are inclined relative to one another, said awl distal portion having a pointed end opposite said awl proximal portion; and a guide jig including
a template having a guide bore,
a means for anchoring said template to the outer surface of a bone, and
a means for manipulating said template to apply said anchoring means to the bone outer surface such that said guide bore is adjacent to a preselected entry point on the bone outer surface and the longitudinal central axis of said guide bore intersects the entry point, said guide bore radially supporting said awl distal portion inserted through it to direct the awl to puncture the bone outer surface at the entry point,
said template manipulating means including a shank having distal and proximal portions the longitudinal central axes of which are inclined relative to one another, said manipulating distal portion being fixed to said template such that, when said awl distal portion is inserted through said guide bore, the proximal portion of said awl and the proximal portion of said template manipulating means are laterally offset from the longitudinal central axis of said guide bore enabling manipulatingly grasping of said awl and guide jig remote from the bone and surrounding soft tissue.

12. An intramedullary awl kit according to claim 11 wherein said anchoring means has an anchor axis about which said template rotates relative to the bone when said template is anchored to the bone outer surface, said anchoring means limiting translation of said template relative to the bone outer surface in a plane perpendicular to said anchor axis when said template is anchored to the bone outer surface.

13. An intramedullary awl kit according to claim 12 wherein said anchoring means comprises an elongate anchoring tip fixed to the surface of said template which, when said template is anchored to the bone outer surface, faces the bone outer surface, the longitudinal central axis of said anchoring tip being perpendicular to the adjoining surface of said template and defining said anchor axis, said anchoring tip having a pointed end, said template being anchored to the bone by driving said anchoring tip into the bone outer surface.

14. An intramedullary awl kit according to claim 13 wherein said anchoring tip defines a central anchoring tip, said anchoring means further comprising an elongate outer anchoring tip fixed to the surface of said template which, when said template is anchored to the bone outer surface, faces the bone outer surface, the longitudinal central axes of said outer and central anchoring tips being parallel to one another, said outer anchoring tip having a pointed end and a shorter length relative to the length of said central anchoring tip, said template being further anchored to the bone by driving said outer anchoring tip into the bone outer surface.

15. An intramedullary awl kit according to claim 14 wherein said anchoring means comprises a plurality of said outer anchoring tips the longitudinal central axes of which are equidistant from the longitudinal central axis of said central anchoring tip.

16. A method for puncturing a non-planar outer surface of a bone comprising the steps of:

positioning, via a manipulation means, a template having two arms each of which has a distal side, the distal sides forming with each other an angle of less than 180°, one of the arms having a guide bore such that the guide bore is adjacent to a preselected entry point of the outer surface of a bone;

applying, via the manipulation means, an anchoring means to the bone outer surface to anchor the other arm of the template to the bone outer surface such that the guide bore remains adjacent to the entry point;

swivelling the template relative to the bone about an anchor axis of the anchoring means when the template is anchored to the bone outer surface to position the guide bore so that its longitudinal central axis intersects the entry point; and inserting a pointed end of a shank of an awl through the guide bore such that the guide bore radially supports the shank to direct it to puncture the entry point on the bone outer surface.

17. A method for puncturing the outer surface of a bone according to claim 16 wherein said applying of the anchoring means to the bone outer surface includes the step of driving an elongate anchoring tip of the anchor means fixed to the template into the bone outer surface, the anchoring tip having a pointed end, the longitudinal central axis of the anchoring tip being perpendicular to the adjoining surface of the template and defining the anchor axis, said swivelling of the template comprises the step of swivelling said template about the longitudinal central axis of the anchoring tip.

18. A method for puncturing the outer surface of a bone comprising the steps of:

positioning, via a manipulation means, a template having a guide bore such that the guide bore is adjacent to a preselected entry point of the outer surface of a bone;

applying, via the manipulation means, an anchoring means to the bone outer surface to anchor the template to the bone outer surface such that the guide bore remains adjacent to the entry point;

swivelling the template relative to the bone about an anchor axis of the anchoring means when the template is anchored to the bone outer surface to position the guide bore so that its longitudinal central axis intersects the entry point; and inserting a pointed end of a shank of an awl through the guide bore such that the guide bore radially supports the shank to direct it to puncture the entry point on the bone outer surface wherein the anchoring means comprises elongate central and outer anchoring tips fixed to the template, the longitudinal central axes of the anchoring tips and guide bore being perpendicular to the adjoining surface of the template, the longitudinal central axis of the central anchoring tip defining the anchor axis, the central anchoring tip having a longer length than the outer anchoring tip, the anchoring tips having pointed ends, said applying of the anchoring means to the bone outer surface and swivelling of the template about the anchor axis including the steps of:

driving an outer portion of the central anchoring tip into the bone such that a clearance remains between the outer anchoring tip and bone outer surface;

swivelling the template relative to the bone about the longitudinal central axis of the central anchoring tip to position the longitudinal axis of the guide bore to intersect the entry point; and driving the inner portion of the central anchoring tip and the outer anchoring tip into the bone.

19. A method for puncturing the outer surface of a bone comprising the steps of:

positioning, via a manipulation means, a template having a guide bore such that the guide bore is adjacent to a preselected entry point of the outer surface of a bone;

applying, via the manipulation means, an anchoring means to the bone outer surface to anchor the template to the bone outer surface such that the guide bore remains adjacent to the entry point;

swivelling the template relative to the bone about an anchor axis of the anchoring means when the template is anchored to the bone outer surface to position the guide bore so that its longitudinal central axis intersects the entry point; and inserting a pointed end of a shank of an awl through the guide bore such that the guide bore radially supports the shank to direct it to puncture the entry point on the bone outer surface and further comprising the steps of:

forming an elongate incision having proximal and distal ends in the outer surface of the soft tissue surrounding the bone outer surface, the incision being laterally positioned relative to the longitudinal central axis of the bone;

spreading the soft tissue between the proximal and distal ends of the incision to provide access to the entry point and surrounding portion of the bone outer surface;

inserting the shank of the awl through the incision, the shank having proximal and distal portions the longitudinal central axes of which are inclined relative to one another and the awl pointed end is formed in the end of the awl distal portion, the inclination between the awl proximal and distal portions enabling a section of the awl proximal portion formed for grasping to remain outside of the soft tissue adjacent to the incision proximal end in a position laterally offset from the longitudinal central axis of the guide bore;

inserting a shank of the manipulating means through the incision, the shank having proximal and distal portions the longitudinal central axes of which are inclined relative to one another and the template is fixed to the end of the manipulating distal portion, the inclination between the manipulating proximal and distal portions enabling the end of the manipulating proximal portion suitable for grasping to remain outside of the soft tissue adjacent to the incision distal end in a position laterally offset from the longitudinal central axis of the guide bore, said forming of the incisions, spreading of the soft tissue, and insertion of the awl and manipulating shanks each being before said positioning of the template; and manipulatingly grasping the awl proximal portion and the manipulating proximal portion outside of the soft tissue for said insertion of the pointed end of the awl shank through the guide bore and said swivelling of the template about the anchor axis.

20. A method for puncturing the outer surface of a bone comprising the steps of:

positioning, via a manipulation means a template having a guide bore such that the guide bore is adjacent to a preselected entry point of the outer surface of a bone;

applying, via the manipulation means, an anchoring means to the bone outer surface to anchor the template to the bone outer surface such that the guide bore remains adjacent to the entry point;

swivelling the template relative to the bone about an anchor axis of the anchoring means when the template is anchored to the bone outer surface to position the guide bore so that its longitudinal central axis intersects the entry point; and inserting a pointed end of a shank of an awl through the guide bore such that the guide bore radially supports the shank to direct it to puncture the entry point on the bone outer surface wherein the shank of the awl has proximal and distal portions the longitudinal axes of which are inclined relative to one another and the awl pointed end is formed in the awl distal portion, and further comprising the step, after puncturing the entry point on the bone outer surface, of:

inserting a first preselected axial section of the distal portion into the bone;

rotating the awl shank to produce a preselected angular displacement of the distal portion about its longitudinal central axis; and inserting a second preselected axial section of the distal portion into the bone.

21. A method for puncturing the outer surface of a bone according to claim 20 wherein said first preselected axial section has a length of from 3 to 5 cm.

22. A method for puncturing the outer surface of a bone according to claim 20 wherein said preselected angular displacement is 90°.

* * * * *